(12) United States Patent
Frey et al.

(10) Patent No.: US 8,067,249 B2
(45) Date of Patent: Nov. 29, 2011

(54) METHOD FOR FUNCTIONALIZING BIOSENSOR CHIPS

(75) Inventors: Alexander Frey, Munich (DE); Franz Hofmann, München (DE); Petra Schindler-Bauer, Vaterstetten (DE)

(73) Assignee: Siemens Aktiengesellschaft, Munich (DE)

( * ) Notice: Subject to any disclaimer, the term of this patent is extended or adjusted under 35 U.S.C. 154(b) by 916 days.

(21) Appl. No.: 11/587,058

(22) PCT Filed: Mar. 18, 2005

(86) PCT No.: PCT/EP2005/002941
§ 371 (c)(1),
(2), (4) Date: Dec. 26, 2007

(87) PCT Pub. No.: WO2005/106478
PCT Pub. Date: Nov. 10, 2005

(65) Prior Publication Data
US 2008/0199974 A1 Aug. 21, 2008

(30) Foreign Application Priority Data
Apr. 21, 2004 (DE) .................. 10 2004 019 357

(51) Int. Cl.
*H01L 21/00* (2006.01)
(52) U.S. Cl. .......................................................... 438/1
(58) Field of Classification Search .............. 438/1, 462; 435/6; 536/23.2, 24.3; 204/403.1, 403.12, 204/403.14
See application file for complete search history.

(56) References Cited

U.S. PATENT DOCUMENTS

| | | | | |
|---|---|---|---|---|
| 4,975,175 A | * | 12/1990 | Karube et al. | 204/403.12 |
| 6,465,329 B1 | * | 10/2002 | Glenn | 438/462 |
| 6,795,192 B2 | | 9/2004 | Dickopf et al. | |
| 6,930,365 B2 | | 8/2005 | Bergaud et al. | |
| 2002/0090649 A1 | | 7/2002 | Chan et al. | |
| 2002/0095073 A1 | | 7/2002 | Jacobs et al. | |
| 2003/0153026 A1 | * | 8/2003 | Alarcon et al. | 435/14 |
| 2003/0186263 A1 | | 10/2003 | Frey et al. | |
| 2004/0046128 A1 | | 3/2004 | Abel et al. | |
| 2004/0094414 A1 | | 5/2004 | Engelhardt et al. | |
| 2004/0096866 A1 | * | 5/2004 | Hofmann et al. | 435/6 |
| 2004/0152091 A1 | | 8/2004 | Paulus et al. | |

(Continued)

FOREIGN PATENT DOCUMENTS

DE  199 16 921 A1  10/2000

(Continued)

OTHER PUBLICATIONS

A.Yu.Rubina et al.: "Hydrogel drop microchips with immobilized DNA: properties and methods for large-scale production", Analytical Biochemistry 325, 2004, pp. 92-106.

(Continued)

*Primary Examiner* — Thomas L Dickey
*Assistant Examiner* — Nikolay Yushin
(74) *Attorney, Agent, or Firm* — Harness, Dickey & Pierce, P.L.C.

(57) ABSTRACT

A method is disclosed for functionalizing biosensors. The biosensors are based on semiconductor chips mounted on a finished processed wafer. They are provided with sensor fields placed thereupon, which are arranged in any array, and, to be precise, for carrying out a functionalization, for example, with organic molecules such as nucleic acids like DNA, RNA and PNA or with their derivatives, proteins, sugar molecules, or antibodies.

21 Claims, 6 Drawing Sheets

U.S. PATENT DOCUMENTS

| | | | |
|---|---|---|---|
| 2004/0234417 A1* | 11/2004 | Schienle et al. | 422/82.08 |
| 2005/0003519 A1 | 1/2005 | Jobst et al. | |
| 2005/0136550 A1* | 6/2005 | Yang et al. | 436/514 |
| 2005/0194250 A1 | 9/2005 | Frey et al. | |
| 2005/0247559 A1 | 11/2005 | Frey et al. | |

FOREIGN PATENT DOCUMENTS

| | | |
|---|---|---|
| DE | 100 15 818 A1 | 10/2001 |
| DE | 100 52 165 A1 | 5/2002 |
| DE | 101 12 778 A1 | 10/2002 |
| DE | 101 39 742 A1 | 3/2003 |
| DE | 102 24 567 A1 | 12/2003 |
| DE | 102 28 125 A1 | 1/2004 |
| DE | 103 12 670 A1 | 10/2004 |
| WO | WO 00/75644 A1 | 12/2000 |
| WO | WO 01/20330 A1 | 3/2001 |
| WO | WO 01/75150 A2 | 10/2001 |
| WO | WO 02/086479 A1 | 10/2002 |

OTHER PUBLICATIONS

R. Thewes et al.: "Sensor arrays for fully electronic DNA detection on CMOS", Tech.Dig.International Solid-State Circuits Conference (ISSCC), 2002, pp. 350-351, pp. 472-473.

A. Frey et al.: "Design of an integrated potentiostat circuit for CMOS biosensor chips", Proc.International Symposium on Circuits and Systems (ISCAS), 2003, pp. V9-V12.

* cited by examiner

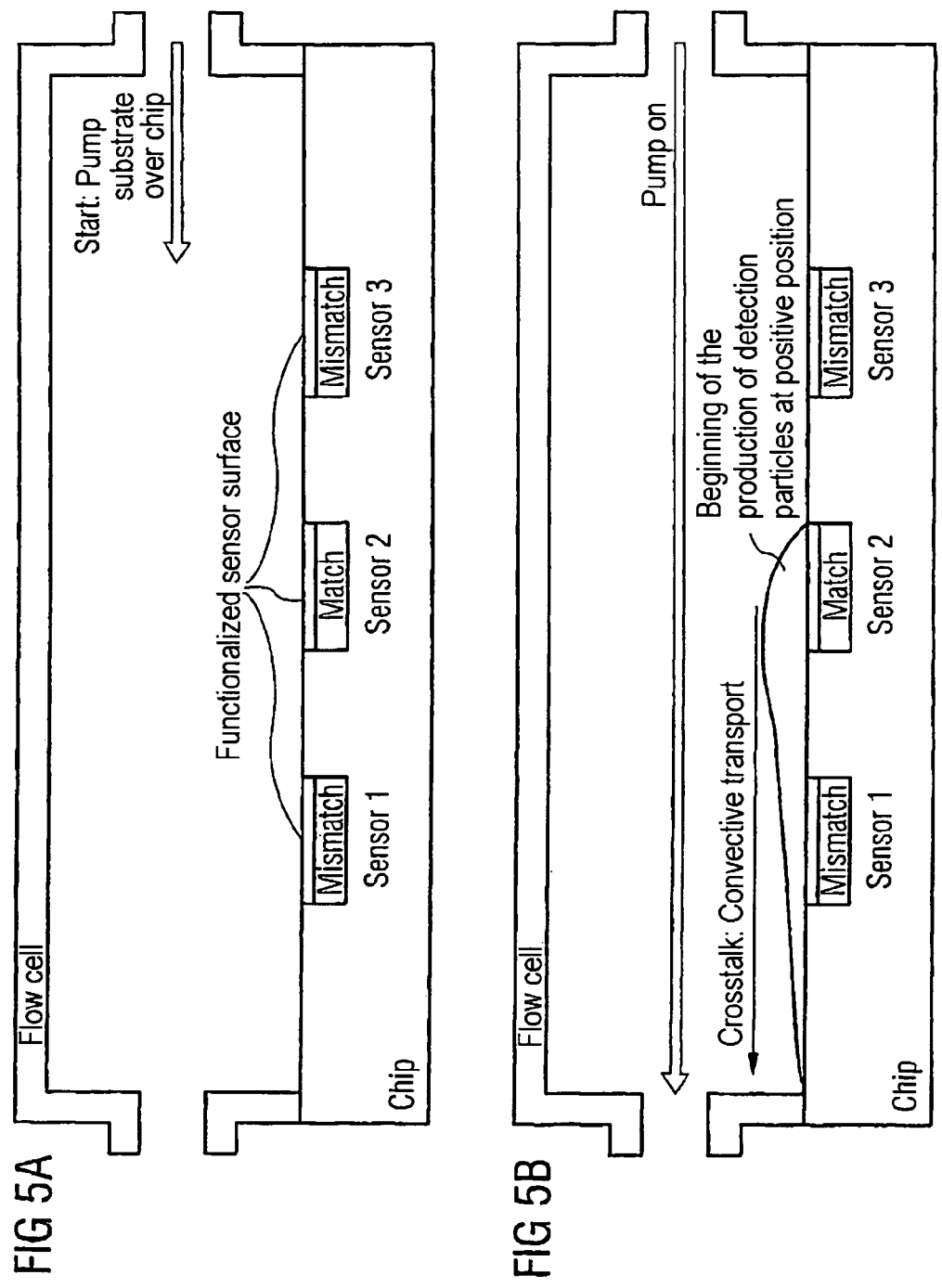

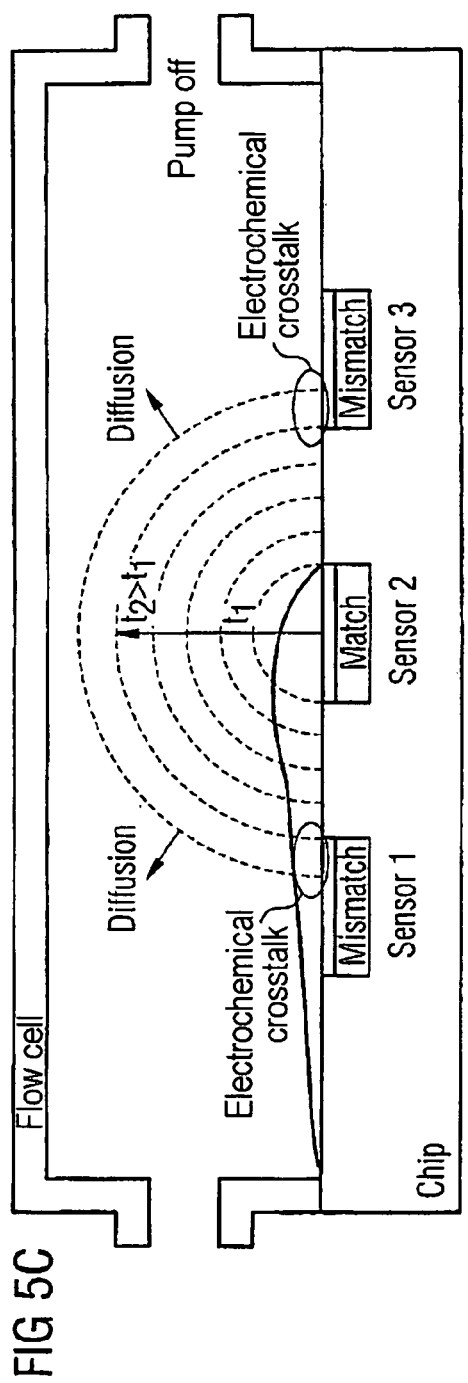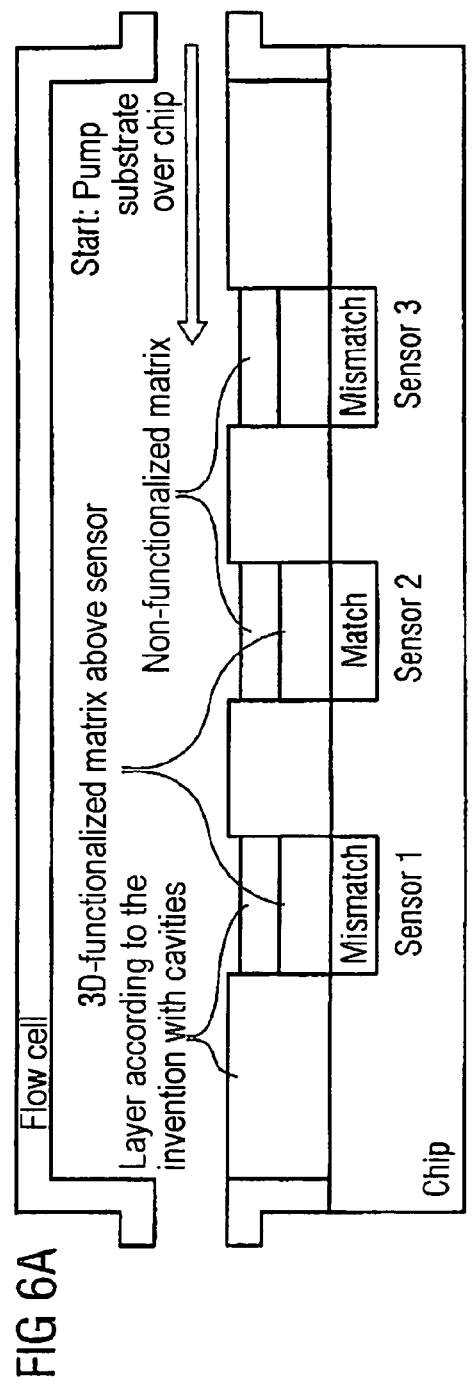

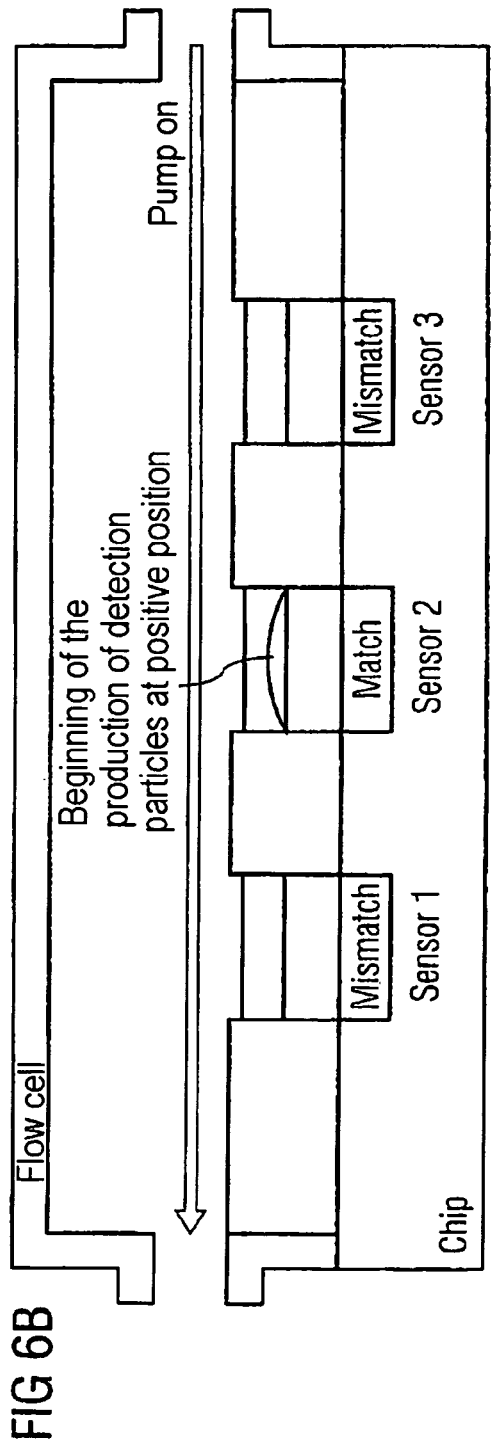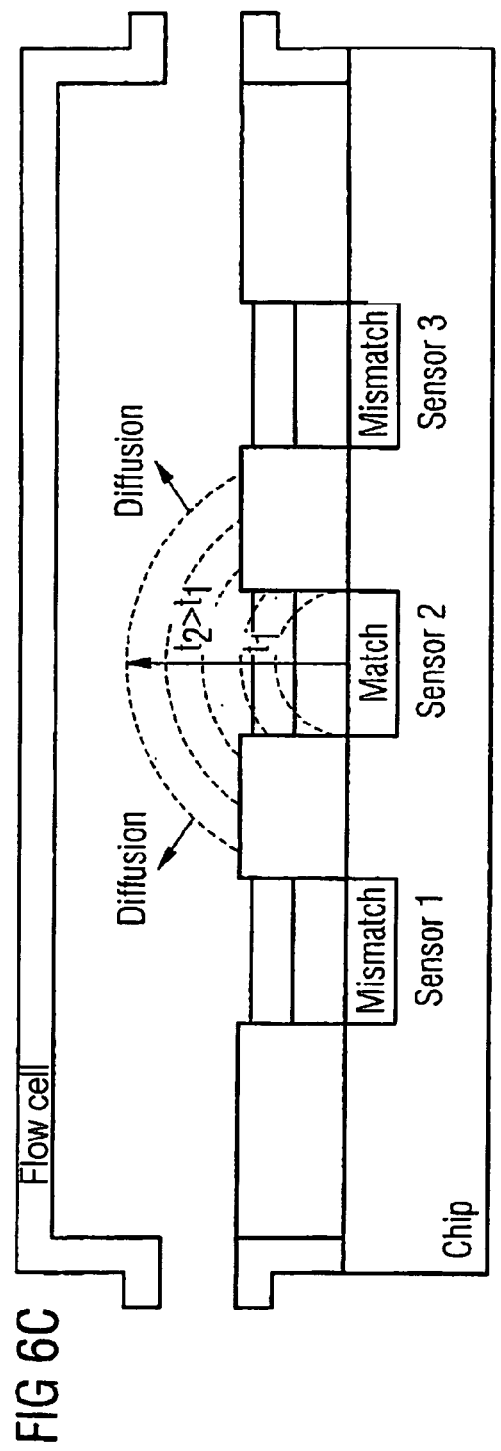

US 8,067,249 B2

METHOD FOR FUNCTIONALIZING BIOSENSOR CHIPS

PRIORITY STATEMENT

This application is the national phase under 35 U.S.C. §371 of PCT International Application No. PCT/EP2005/002941 which has an International filing date of Mar. 18, 2005, which designated the United States of America and which claims priority on German Patent Application number 10 2004 019 357.6 filed Apr. 21, 2004, the entire contents of which are hereby incorporated herein by reference.

FIELD

The present invention generally relates to a method for functionalizing biosensor chips. For example, it may relate to a method functionalizing biosensor chips based on semiconductor chips arranged on a fully processed wafer and including sensor fields, usually arranged in an array format, applied to them, specifically functionalization for example with organic molecules, such as for example nucleic acids, such as DNA, RNA and PNA or their derivatives, proteins, sugar molecules or antibodies.

BACKGROUND

Biosensor arrays are used to detect molecules in an analyte that is to be tested. Arrays of this type are increasingly realized on chips, with a view to miniaturization. The sensors are often arranged in large numbers on a substrate. The high degree of parallelism allows different tests to be carried out in parallel at the same time, for example tests for the presence of different substances (e.g. molecules) in a predetermined analyte. This property indicates that sensor arrangements of this type, including a corresponding evaluation system, have numerous possible applications in medical diagnostics, such as for example in the point-of-care or home-care sector, in the pharmaceutical industry (e.g. for pharmaceutical screening, pharmacogenomics, high throughput screening HTS)), in the chemical industry, in food analysis, in general scientific research, such as for example gene sequencing, and in environmental and food technology.

To functionalize such biosensors or biochips, it is customary for a small quantity of binding-ready capture molecules, also referred to as probes, for example a specific nucleic acid sequence, to be immobilized on the surface of a specifically configured substrate (biochip base module). This immobilization, according to the coupling chemistry used, is usually implemented at the substrate surface in such a manner that the capture molecules remain thereon even in the event of washing processes. Therefore, the basic principle of many known sensors is based on first of all capture molecules of this type being applied to a chip in a position-specific manner, for example using micro-dispensing techniques, and being immobilized using a corresponding binding chemistry. The application is preferably in an array format, in which case, by way of example, different oligonucleotide sequences can be immobilized at different array positions.

By minimizing the dimensions of the individual positions of an array, it is possible on the one hand to increase the array density and on the other hand to improve the sensitivity of detection. Then, by way of example, highly parallel DNA analyses can be carried out by means of a DNA microarray formed in this way. The analyte molecules to be tested, such as for example nucleic acids, are usually marked and hybridized with the capture molecules such as for example nucleic acids, on the chip. Hybridization generally takes place only between exactly complementary nucleic acid molecules. The intensity of the signal measured is usually proportional to the quantity of hybridized sample.

The abovementioned arrays have in recent years also been realized on an industrial scale in a biochip with integrated electronic evaluation technology. A biochip of this type allows fast, simple and inexpensive analysis of biomolecules, such as for example the abovementioned nucleic acids or proteins, in clinical diagnostics and patient-individual medicine. A biochip of this type or its base module may, for example, contain a multiplicity of miniaturized sample holders or sensor elements with metal electrodes, such as for example gold electrodes, which are arranged in an interdigital structure and to which biomolecules can in each case be applied. The evaluation is then effected using extremely small current profiles. Biochips of this type are based on a standard CMOS (Complementary Metal Oxide Semiconductor) semiconductor fabrication process with additional gold electrodes.

However, one drawback of the fabrication of biosensors of this type is that to date functionalization of semiconductor chips, for example with organic molecules, such as DNA or proteins, has not been possible at wafer level, since the functional layer, i.e. the layer which comprises the capture molecules, cannot be preserved for a prolonged period of time and is often destroyed during singulation, i.e. when the chips are being sawn out. Moreover, the application of a defined quantity of functional molecules for functionalizing the sensor fields is problematic, in that divergent flow on the part of the liquid quantity reduces the concentration, and if the liquid quantities flow into one another sensor signal crosstalk occurs.

A further drawback is that a complex but ultimately inadequate cleaning procedure has to be carried out prior to the functionalization. Another problem of the biosensors available in the prior art is the occurrence of offset currents, caused by unspecific reactions, during electrochemical reading.

To overcome the abovementioned problems, at present, after singulation, the chips are cleaned and functionalized individually by hand, which is expensive. However, such handling cannot be implemented on a large industrial scale.

SUMMARY

At least one embodiment of the present invention includes a method which allows functionalization of biosensors at wafer level without having or causing at least one of the problems explained above. In at least one further embodiment, a biochip is provided which, in particular when used in assay methods, should not be subject to offset currents, caused by unspecific reactions, during electrochemical reading.

In at least one embodiment, a method is provided for functionalizing a biosensor, comprising:
(i) providing a substrate, which has a large number of sensor fields arranged thereon,
(ii) applying a layer which has been patterned in a predetermined way, with the result that a corresponding cavity is formed above the sensor fields, and
(iii) applying capture molecules to the sensor fields, so that the capture molecules are immobilized within the cavity above the sensor fields.

In the context of the method according to at least one embodiment of the invention, the application of a layer which has been patterned in a predetermined way and is usually based on an organic polymer leads to the formation of cavities above the sensor fields that are to be functionalized, which cavities can subsequently function as compartments. Capture molecules which are used for functionalization, e.g. DNA molecules, can be introduced into these compartments.

The substrate used in step (i) may be a ceramic substrate, a semiconductor substrate (in particular a silicon substrate i.e. a silicon wafer or a silicon chip), a glass substrate or a plastic substrate.

According to an example embodiment of the present invention, in step (i) the substrate used is a fully processed wafer having at least one semiconductor chip, at least one sensor field, usually in each case two or more sensor fields, being arranged on the semiconductor chip. In an advantageous configuration of an embodiment of the biosensor, the electrical recording circuit is integrated in the semiconductor chip, which has the advantage that as a result the overall measurement structure can be simplified and a higher measurement sensitivity is achieved. Further simplification results from a configuration in which the sensor fields are arranged on the semiconductor chip.

The semiconductor chip used can in principle be any suitable semiconductor component. It is preferable to use a transistor chip, which may be a CMOS chip.

In the context of at least one embodiment of the present invention, the term "sensor field" is to be understood as meaning an arrangement or surface on or by which the capture molecules can be immobilized, i.e. to which the capture molecules can bind or are coupled by physical or chemical interactions. These interactions include hydrophobic, hydrophilic, von der Waals or ionic (electrostatic) interactions and covalent bonds. It is preferable for the sensor field to have an electrically conductive surface. Examples of suitable surface materials which can be used for the sensor field include metals, such as for example gold, platinum or palladium, or electrically conductive polymers.

In an embodiment of the present invention, a sensor field preferably represents an electrode or a component of an electrode. The immobilization of a sensor field can take place in such a manner that the entire surface of a field is provided with capture molecules for immobilization purposes. However, it is also possible for the immobilization to be selectively restricted to individual regions/spots of a field for immobilization purposes.

To achieve the latter option, the sensor field can be correspondingly configured, for example by means of regions which have been chemically activated for the immobilization. In one embodiment of the present invention, the capture molecules are bound or coupled to the sensor surface directly, i.e. without the provision of a further layer, such as a carrier layer as described below.

The sensor field may be an electrochemical sensor field or an impedance sensor field. If the sensor field is an electrochemical sensor field, it may be configured in particular as a redox recycling sensor field. In the case of a redox recycling sensor field, particles or targets which are to be recorded are usually provided with an enzyme label, which after a hybridization event has taken place with capture molecules immobilized on the sensor field, is used to split an electrochemically inactive substance that is to be introduced into the arrangement into two molecule parts, at least one of which is electrochemically active. This leads to a change in the electrical properties of the respective sensor position in the corresponding biosensor array.

In an example embodiment of the present invention, the sensor fields are set up as interdigital electrode fields, for example gold, platinum or palladium.

In step (ii) of the method according to an embodiment of the invention, the layer which has been patterned in a predetermined way is usually applied in a thickness in the range from 10 to 300 µm. Depending on the predetermined sensor fields, the cavities or compartments produced usually have a diameter in the range from 10 to 300 µm. In an example embodiment of the present invention, in step (ii) first of all a photoresist layer is applied over the entire surface of the substrate, and then the photoresist layer is photolithographically patterned using a photomask with a predetermined pattern, with the result that a corresponding cavity is formed above the sensor field. There are no specific restrictions on the type of photoresist. However, it is preferable for the photoresist to be a negative UV photoresist of the epoxy type. Photoresists of this type are available under the trade name SU-8 or THB-430N. After exposure using a correspondingly patterned mask, corresponding cavities or compartments are formed above the sensor fields, with a height or depth corresponding to the thickness of the photoresist layer.

Alternatively, the layer which has been patterned in a predetermined way can be applied in the form of a three-dimensional organic polymer matrix by microcontact printing or microcontact stamping or soft lithography, as is known from the prior art. The polymer matrix may for example be composed of epoxy resin, polyolefins, such as polypropylene, poly(meth)acrylates, fluoropolymers, such as for example Teflon, polysiloxanes or polyimide.

According to one embodiment of the present invention, prior to the actual functionalization of the sensor fields, i.e. prior to step (iii), a carrier layer, preferably based on hydrogel, in particular based on poly(meth)acrylamide gel, can be applied to the sensor fields. In this case, the application of capture molecules to the sensor fields in step (iii) can in particular also be carried out with simultaneous application of a carrier layer, preferably based on hydrogel, in particular based on poly(meth)acrylamide gel, to the sensor fields.

The use of carrier layers of this type is known in the prior art; cf. for example A.Yu.Rubina, Analytical Biochemistry, 325 (2004), pages 92-106. In this case, first of all acrylamide groups or methacrylamide groups are introduced for example into the terminal 3' or 5' position of DNA molecules, followed by the polymerization of precursors of this type so as to form a hydrogel, in or to which capture molecules, such as for example DNA molecules, are covalently bonded. In such a situation, the capture molecules, such as for example DNA molecules, are not bound or coupled directly to the sensor fields, but rather are immobilized in a corresponding carrier layer, preferably based on hydrogel, above the respective sensor field.

In step (iii) of the method according to an embodiment of the invention, the application of capture molecules, such as for example nucleic acids, proteins, sugar molecules, antibodies, etc., in particular oligonucleotide probes, to the sensor fields, takes place in such a way that the capture molecules are immobilized within the cavity, produced by the layer that has been patterned in a predetermined way, in particular a correspondingly patterned photoresist layer, above the sensor fields. This can be carried out either on a suitable sensor surface or by way of a three-dimensional matrix, e.g. hydrogel. This operation can particularly advantageously take place in automated fashion at wafer level. If the sensor field is provided in the form of a gold electrode, the immobilization of the capture molecules can be realized using the particularly advantageous gold-sulfur coupling which is known from biochemistry, for example by a thiol end group of the capture molecules being chemically coupled to the gold electrode.

It should be noted that it is of course possible to use an example embodiment of the present method to record not just a single type of nucleic acid in a single series of measurements. Rather, it is possible for a plurality of nucleic acids to be recorded simultaneously or in succession. To this end, a plurality of types of capture molecules, each of which has a (specific) binding affinity for a specific nucleic acid that is to be recorded, can be bound on the sensor fields, and/or a plurality of units can be used for immobilization, with just one type of capture molecule being bound to each of these units. With these multiple determinations, it is preferable for a marker which can be distinguished from the other markers to be used for each nucleic acid to be recorded, in order in this way for example to avoid undesired secondary reactions.

To be used for a multiple determination of this type, the biosensor preferably has a plurality of, i.e. more than two, sensor fields for immobilizing nucleic acids in a regular arrangement.

Step (iii) may optionally be followed by the application of an encapsulation layer, preferably based on hydrogel, in particular based on poly(meth)acrylamide gel.

If, within the scope of the method according to an embodiment of the invention, a fully processed wafer with semiconductor chips arranged thereon is used, with the sensor fields in each case arranged on the semiconductor chips, the wafer which has been functionalized in this manner following step (iii) can be arranged in upside-down mode on a sawing sheet which has been tensioned in a sawing frame, such as for example a Mylar® sheet which is customarily used for such purposes, after which the individual chips are sawn out of the wafer using standard techniques. The sawing of the wafer takes place in what is known as upside-down mode, i.e. with the underside of the wafer facing upward. Prior to the singulation of the chips, the sheet can be removed again without leaving any residues, typically after UV exposure or heat treatment, so that the functional layer is directly available to the user. The application according to the invention of a photoresist layer, and the resulting formation of corresponding cavities or compartments, protects the functional layer in the compartments from mechanical damage and contamination, so that it is preserved for a longer period of time.

Furthermore, by the use of an embodiment of the method described, complex chemical cleaning of the sensor surfaces (for example using cyanides) to reduce sawing dust is no longer necessary. Divergent flow, resulting in a reduction in concentration, of the functional molecules to be applied is likewise prevented by the compartmentalization achieved using the method of an embodiment of the present invention, as is the problem of the molecules flowing into one another (crosstalk). Therefore, the method according to an embodiment of the invention can be used to introduce an accurately defined quantity of functional molecules into each compartment. If three-dimensional carrier materials such as hydrogels, are additionally used, it is possible to additionally increase the quantity of functional molecules per sensor field. It is therefore easier to increase the density of sensor fields per unit area.

At least one embodiment of the present invention also relates to a biosensor chip, comprising a substrate with at least one semiconductor chip arranged thereon, at least one sensor field in turn being arranged on the semiconductor chip, at the bottom of a cavity which is surrounded by a layer that has been patterned in a predetermined way, in particular a photoresist layer, and has been fully applied over the entire surface of the semiconductor chip, a functional layer, comprising capture molecules, being immobilized in the cavity above the sensor field. A chip of this type can be produced using the method outlined above. A biosensor chip of this type may also include a control circuit, an electrical recording device or an evaluation circuit. Furthermore, if necessary, it is also possible to provide a temperature monitoring and control device, such as for example a heat sensor. In this respect, reference is made for example to the content of disclosure of DE 102 24 567 A1, DE 102 28 125 A1 and DE 101 12 778 A1.

At least one embodiment of the present invention also relates to the use of a layer based on an organic polymer, which has been patterned with recesses or cavities and is arranged above a sensor field of a biosensor, in particular a photoresist layer, for immobilizing a functional layer, comprising capture molecules, on or above the sensor field.

BRIEF DESCRIPTION OF THE DRAWINGS

In the drawing:

FIG. 5 schematically depicts the problem of the production of non-specific signals, as occurs with biosensors of the prior art.

FIG. 6 schematically depicts how the problem of the production of non-specific signals can be overcome by the biosensors produced in accordance with an embodiment of the invention.

DETAILED DESCRIPTION OF THE EXAMPLE EMBODIMENTS

FIG. 1 schematically depicts the production of individual biosensor chips by way of the method according to an embodiment of the invention for the situation in which in the method according to an embodiment of the invention the substrate used is a fully processed wafer (10) with semiconductor chips (20) arranged thereon. Sensor fields (30) in each case being arranged on the semiconductor chips; cf. FIG. 1a). Then, a photoresist layer (40) is applied over the entire surface of the wafer, for example by means of a spin-coating, etc.; cf. FIG. 1b).

Figure 1A:
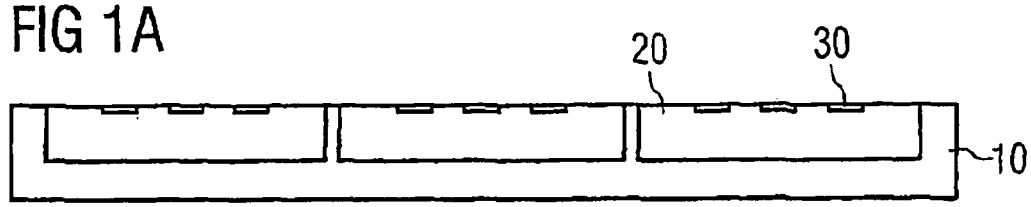
FIG. 1 schematically depicts the production of individual biosensor chips by way of an example embodiment of the method according to the invention.
Figure 1B:
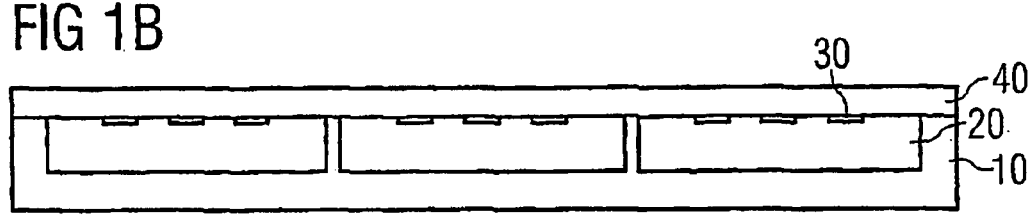
Figure 1C:
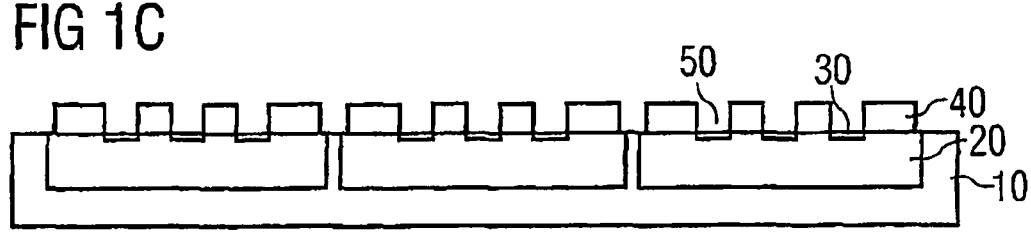
Figure 1D:
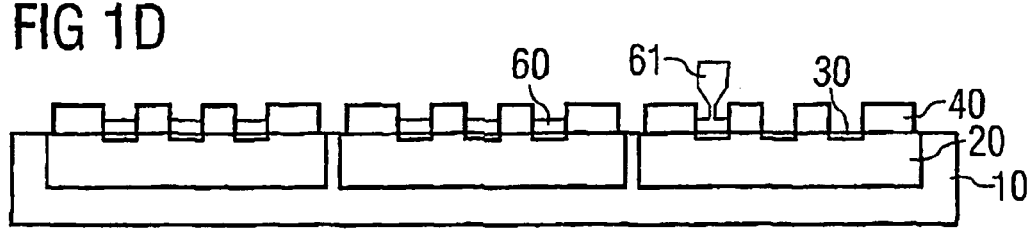
Figure 1E:
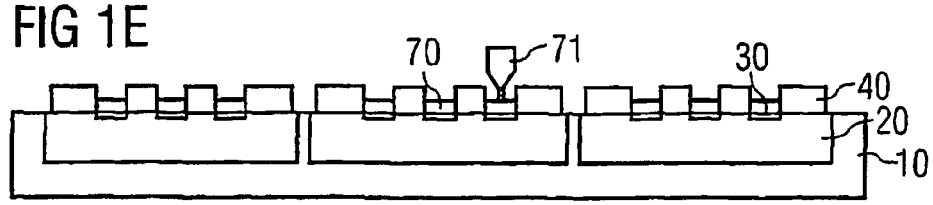
Figure 1F:
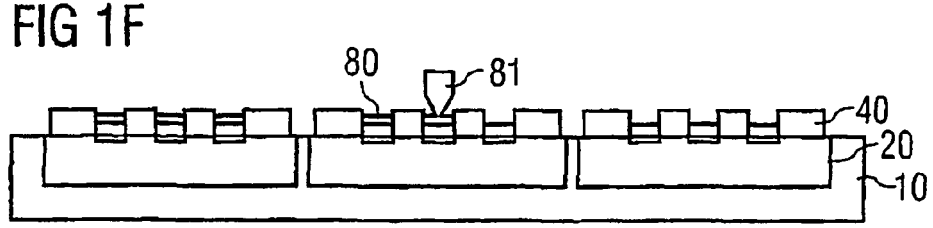
Figure 1G:
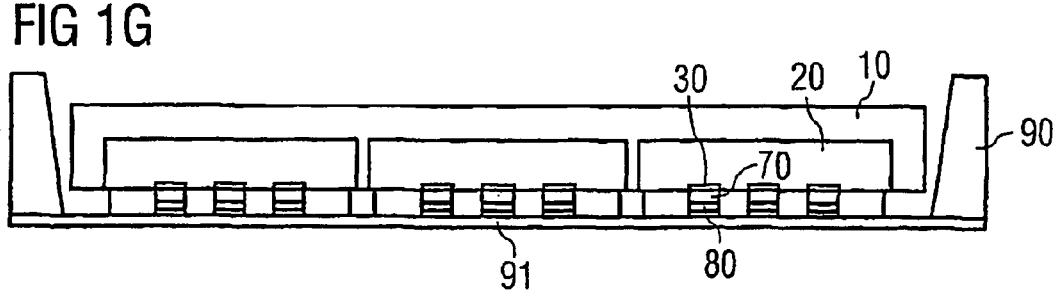
Figure 1H:
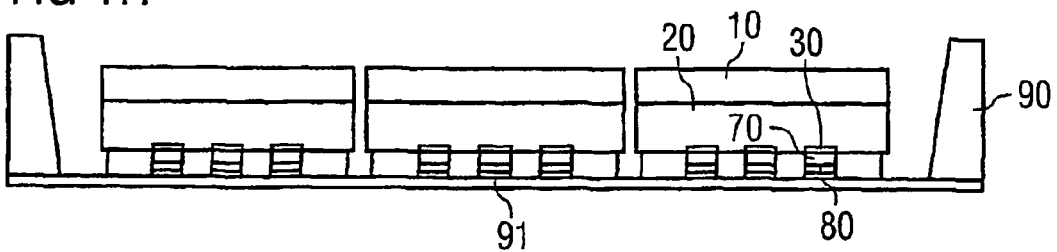
Figure 2:
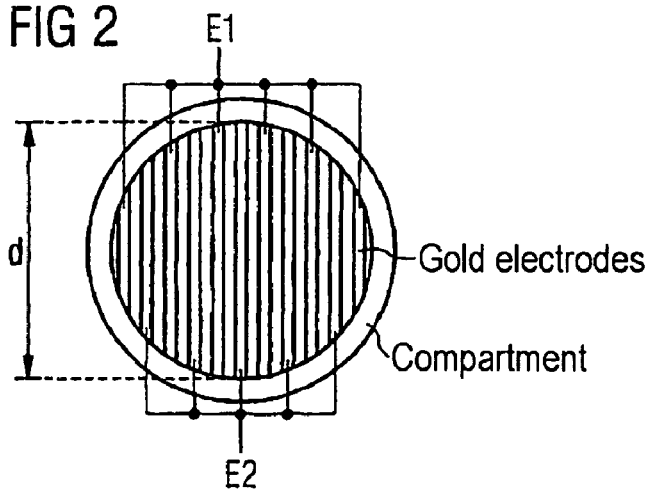
FIGS. 2, 3 and 4 schematically depict the sensor principle of an example embodiment of a biosensor chip produced using the method of an embodiment of the present invention, FIG. 2 showing a plan view of a compartment above an interdigital gold electrode arrangement, FIG. 3 schematically depicting how a corresponding current is generated in a biomolecule detection method based on "redox recycling", and FIG. 4 reproduces the output signal produced.

After the patterning of the photoresist by use of a corresponding photomask (cf. FIG. 1c)), during which sensor fields (60) and sawing frame are freely exposed and corresponding compartments (50) are formed above the sensor fields, it is optionally possible first of all to apply a carrier layer (60), for example based on hydrogel, to the sensor fields (30) in order to form a 3D matrix, for example by way of spotting; cf. FIG. 1d). This is followed by the functionalization, i.e. the immobilization of capture molecules so as to form the actual functional layer (70) above the sensor fields (30); cf. FIG. 1e). This may optionally be followed by the application of an encapsulation layer (80), for example based on hydrogel; cf. FIG. 1f). The application of the carrier layer and of the functional layer may also be carried out simultaneously. Then, the wafer is arranged, with the functionalized side facing downward (upside-down mode), on a sawing sheet (91) which is tensioned inside a sawing frame (90); cf. FIG. 1g). Finally, the biosensor chips are sawn out of the wafer; cf. FIG. 1h).

Figure 3:
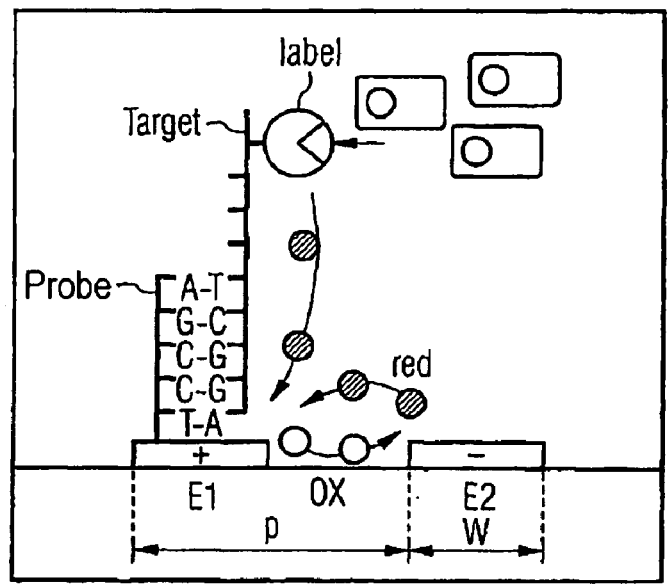
Figure 4:
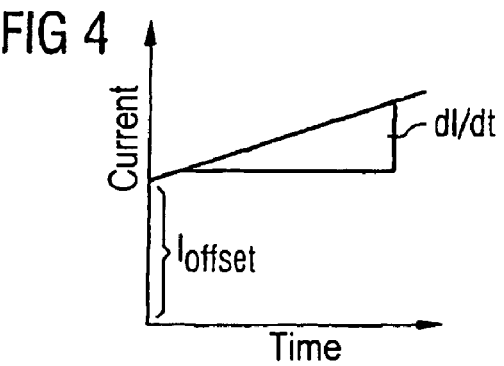

The text which follows explains further advantages, which arise in particular for electrochemical detection methods in which convection and diffusion processes take place. One example of a biomolecule detection method of this type is the "redox recycling" illustrated in FIG. 3.

DNA with a specific sequence has been immobilized on each surface of a pixel of the sensor field. After the hybridization, pixels with double-stranded DNA are to be found. A label is usually coupled to the target DNA strand. Substrate particles are converted into redox-active species with the aid of the enzyme label and diffused to the electrodes. There, a redox process is initiated by application of suitable potentials, producing a specific signal; cf. also R. Thewes et al, "Sensor arrays for fully electronic DNA detection on CMOS", Tech. Dig. International Solid-State Circuits Conference (ISSCC), 2002, pages 350-351 and 472-473 and A. Frey et al., "Design of an integrated potentiostat circuit for CMOS biosensor chips", Proc. International Symposium on Circuits and Systems (ISCAS), 2003, pages V9-V12.

However, problems arise in that the redox particles cannot be found specifically only in the vicinity of the label which generates them. There may be a number of reasons for this. A first reason for the non-specific presence of redox particles lies in the reaction equilibrium between substrate and redox particles. For example, inter alia a non-enzymatic spontaneous hydrolysis of the substrate may occur. A second reason lies in the test sequence. The substrate particles are fed to the sensor chip using a pump, i.e. in a flow (cf. FIG. 5a). As soon as substrate is present, redox particles are formed at the sensor positions with a match (i.e. the presence of enzyme labels). During this phase, these particles are distributed over the entire chip by convection and are therefore likewise non-specific (cf. FIG. 5b). A further reason for non-specific redox particle concentrations is the gradient-driven diffusion, for example between adjacent pixels with match and mismatch, as illustrated in FIG. 5c).

The non-specific redox particle concentrations described are particularly critical if they are high compared to the concentration to be detected. The result is a total concentration of detection particles which is translated into a non-specific sensor current component. This offset component can limit the signal resolution and therefore form a lower limit on the dynamic range.

FIG. 6 illustrates how the above-described problem of non-specific signals can be avoided or significantly reduced with the aid of the cavities produced according to the invention. FIG. 6a) shows a first layer (carrier layer) which is located in the cavities and serves as a 3D functionalization matrix. Above this first layer is a second layer (encapsulation layer) as a diffusion barrier, for example made from the same material but without functionalization (no DNA capture molecules in this layer). The second layer may also consist of a different material than the first layer, in order to allow certain properties to be set in an advantageous way (e.g. diffusion constant for substrate and redox particles).

If the substrate material is then pumped over the chip, the start of production of the redox particles is delayed on account of the second layer. The delay time can to a certain extent be set with the aid of the thickness of the second layer and material properties which influence the diffusion constant of the substrate particles.

A further important time interval is the period during which the redox particles produced are still inside the cavities. If the pump flow is stopped within the sum of the times described above, the non-specific crosstalk caused by convection is suppressed. The diffusion-driven electrochemical crosstalk is likewise prevented or at least reduced, as illustrated in FIG. 6c). The diffusion-impeding action of the second layer and the geometric shielding of the cavities are advantageous in this respect.

In addition to the above-described suppression of non-specific signals, the cavities, together with the two layers, also amplify the sensor signal, since the redox particles specifically produced in spatial terms are better able to remain concentrated above the location of the electrochemical reaction. In this way, a signal loss caused by diffusion is reduced. Overall, therefore, the signal-to-noise ratio is improved.

The method according to an embodiment of the invention in summary has the following advantages:
  functionalization of the sensor surfaces in automated fashion at wafer level is possible
  protection from mechanical damage
  protection from contamination
  no longer any need for a complex chemical cleaning procedure prior to the functionalization
  the functional layer can be preserved for a longer period of time
  there is no divergent flow of the functional layer
  it is possible to apply accurately defined quantities of molecules
  the functional layer does not flow together and therefore there is no signal crosstalk
  reduction in dissociation, diffusion and convection, and suppression of the non-specific signal component
  optional inclusion of an artificial diffusion barrier (encapsulation layer)
  improvement of the signal-to-noise ratio
  amplification of the sensor signal
  reduction in the number of sensor fields is possible
  reduction in the offset signal
  universally usable on active/passive chips in array format with optical or electronic reading and coating of any type
  can be adapted for both active and passive chips and for methods with and without label.

The method according to an embodiment of the invention can be used for both industrial or laboratory-scale production of electrically active or passive semiconductor or other chips with functional layers, such as for example nucleic acids, proteins, sugars, antibodies or other chemical and biological layers (chemosensors, biochips). The compartments produced in accordance with the invention can also be used as mini-reaction vessels, e.g. for PCR, cell culture growth, or the like, if appropriate equipped with temperature monitoring and control device(s) and microfluidic stirring system(s).

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF DESIGNATIONS

10 Wafer
20 Semiconductor chip
30 Sensor field
40 Photoresist
50 Cavity
60 Carrier layer, for example based on hydrogel
61 Device for applying the carrier layer
70 Functional layer, comprising capture molecules 71 Device for applying the functional layer or capture molecules
80 Encapsulation layer, for example based on hydrogel
81 Device for applying the encapsulation layer
90 Sawing frame
91 Sawing sheet

The invention claimed is:

1. A method for functionalizing a biosensor, comprising:
providing a substrate, including at least one sensor field arranged thereon:
applying a photoresist layer over an entire surface of the substrate and then photolithographically patterning the photoresist layer using a photomask with a set pattern, so that a patterned layer is formed, to form a corresponding cavity above the sensor filed;
applying capture molecules to the sensor field, so that the capture molecules are immobilized within the cavity above the sensor filed, wherein prior to the application of capture molecules, a carrier layer based on hydrogel is applied to the sensor field, wherein the application of capture molecules the sensor field is carried out simultaneously with the application of a carrier layer based on hydrogel to the sensor field, and wherein the application of capture molecules is followed by application of an encapsulation layer based on hydrogel; and
mounting a wafer, functionalized in such a manner following the application of capture molecules in upside-down mode to a sawing sheet, tensioned in a sawing frame, and sawing individual chips out of the wafer.

2. The method as claimed in claim 1, wherein the sensor filed is set up as an integrated electrode field made from at least on of gold, platinum and palladium.

3. The method as claimed in claim 1, wherein the carrier layer is based on poly(meth)acrylamide gel.

4. The method as claimed in claim 1, wherein sensor field is set up as an integrated electrode field.

5. The method as claimed in claim 4, wherein the photoresist layer is applied in a thickness in the range from 10 to 300 µm.

6. The method as claimed in claim 1, wherein the photoresist layer is applied in a thickness in the range from 10 to 300 µm.

7. The method as claimed in claim 6, wherein the photoresist layer is a negative UV photoresist of an epoxy type.

8. The method as claimed in claim 1, wherein the substrate provided is a fully processed wafer having at least one semiconductor chip, the at least one sensor field being arranged on the semiconductor chip.

9. The method as claimed in claim 8, wherein an electrical recording circuit is integrated in the semiconductor chip.

10. The method as claimed in claim 9, wherein the sensor filed is set up as an integrated electrode field.

11. The method as claimed in claim 9, wherein the sensor filed is set up as an integrated electrode field made from at least on of gold, platinum and palladium.

12. The method as claimed in claim 9, wherein the photoresist layer is applied in a thickness in the range from 10 to 300 µm.

13. The method as claimed in claim 8, wherein the semiconductor chip is a CMOS chip.

14. The method as claimed in claim 9, wherein the semiconductor chip is a CMOS chip.

15. The method as claimed in claim 8, wherein the sensor field is set up as an integrated electrode field.

16. The method as claimed in claim 8, wherein the sensor filed is set up as an integrated electrode field made from at least on of gold, platinum and palladium.

17. The method as claimed in claim 8, wherein the photoresist layer is applied in a thickness in the range from 10 to 300 µm.

18. The method as claimed in claim 8, wherein the carrier layer is based on poly(meth)acrylamide gel.

19. The method as claimed in claim 13, wherein the sensor filed is set up as an integrated electrode field.

20. The method as claimed in claim 13, wherein the sensor filed is set up as an integrated electrode field made from at least on of gold, platinum and palladium.

21. The method as claimed in claim 4, wherein the photoresist layer is applied in a thickness in the range from 10 to 300 µm.

* * * * *